United States Patent [19]

Walter et al.

[11] Patent Number: 5,102,792

[45] Date of Patent: Apr. 7, 1992

[54] SELECTIVE PRODUCTION OF L-SERINE DERIVATIVE ISOMERS

[75] Inventors: James F. Walter, Ashton; Christopher Bull, Bethesda, both of Md.

[73] Assignee: W. R. Grace & Co.-Conn., New York, N.Y.

[21] Appl. No.: 84,782

[22] Filed: Aug. 13, 1987

[51] Int. Cl.$^5$ .............................................. C12P 13/06
[52] U.S. Cl. ..................................................... 435/116
[58] Field of Search ................................ 435/106–110, 435/113, 115–116; 562/444

[56] References Cited

U.S. PATENT DOCUMENTS

| | | | |
|---|---|---|---|
| 3,871,958 | 3/1975 | Nakazawa et al. | 195/29 |
| 4,172,846 | 10/1979 | Boesten | 260/558 A |
| 4,605,759 | 8/1986 | Mita et al. | 562/444 |
| 4,710,583 | 12/1987 | Chmurny et al. | 560/40 |

FOREIGN PATENT DOCUMENTS

| | | |
|---|---|---|
| 220923 | 10/1986 | European Pat. Off. . |
| 54-3952 | 2/1979 | Japan . |
| 2130216 | 5/1984 | United Kingdom . |

OTHER PUBLICATIONS

Nucleic Acids Res. (Plamann et al.), vol. 11, pp. 2065–2075 (1983).

J. Bacteriology (Schirch et al.), vol. 163, No. 1, pp. 1–7 (1985).
Trends in Biotechnology (Hamilton et al.), vol. 3, No. 1, pp. 64–68 (1985).
Biochemistry (Ulevitch et al.), vol. 16, No. 24, pp. 5342–5350 and 5356–5369 (1977).
Biochemistry (Ching et al.), vol. 18, No. 5, pp. 821–829 (1979).

*Primary Examiner*—Douglas W. Robinson
*Assistant Examiner*—S. Saucier
*Attorney, Agent, or Firm*—Vanessa L. Appleby; Steven T. Trinker

[57] ABSTRACT

L-Serine derivatives produced by the enzyme catalyzed aldol condensation of glycine and an aldehyde in aqueous solution are recovered in high yield by extracting the aqueous product solution containing said serine derivatives with an organic phase comprising (i) an aldehyde, or (ii) mixtures of an aldehyde and a water immiscible organic solvent, followed by re-extracting the organic phase with an aqueous phase having a pH of less than about 7.0. The L-erythro isomers of L-serine derivatives such as L-phenylserine may be preferentially prepared by the use of this extraction/re-extraction procedure in combination with bioreactor reaction conditions which include a pH of from about 7.5 to 10, an aldehyde concentration of from about 1 to about 90 grams/liter, a glycine concentration of from about 10 to about 300 grams/liter, and a molar ratio of glycine to aldehyde of from about 4:1 to about 100:1.

25 Claims, 2 Drawing Sheets

EXTRACTOR REACTOR
BENZALDEHYDE

SELECTIVE PRODUCTION OF L-SERINE DERIVATIVE ISOMERS

BACKGROUND OF THE INVENTION

The present invention relates to an improved process for the enzymatic preparation of L-serine derivatives by the aldol condensation of glycine with an aldehyde. It further relates to an improved process for the preparation of such L-serine derivatives whereby synthesis of the L-erythro isomer of such serine derivatives may be selectively obtained. While the present invention is thus concerned with the preparation of L-serine derivatives, it also may be used to advantage in the aldol condensation of glycine with formaldehyde to produce L-serine. Accordingly as used herein, the term "L-serine derivative" includes L-serine itself as well as the various derivatives defined hereinafter in formula (I).

Serine hydroxymethyltransferase (alternatively referred to for the purposes of the subject application as "SHMT") is widely distributed in both eucaryotes and procaryotes and has been isolated from the livers of a variety of mammals and from various bacteria such as *Escherichia coli* and *Clostridium cylindrosporum*. Genetically engineered microorganisms which overproduce this enzyme in large quantities and thereby facilitate the preparation of pure enzyme have also been reported in the literature. See, Plamann et al., *Nucleic Acids Res.*, Vol. 11, pages 2065-2075 (1983), Schirch et al., *J. Bacteriology*, Vol. 163, No. 1, pages 1-7 (1985), and Hamilton et al., *Trends in Biotechnology*, Vol. 3, No. 1, pages 64-68 (1985).

SHMT from a variety of different sources has been reported to catalyze the reversible cleavable of beta-phenylserines, including L-erythro-beta-phenylserine, to benzaldehyde (or substituted benzaldehyde) and glycine. See, Ulevitch et al., *Biochemistry*, Vol. 16, No. 24, pages 5342-5350 and 5356-5369 (1977); Schirch et al., *J. Bacteriology*, Vol. 163, No. 1, pages 1-7 (1985); and Ching et al., *Biochemistry*, Vol. 18, No. 5, pages 821-829 (1979).

In Nakazewa et al., U.S. Pat. No. 3,871,958, there is disclosed a process for the preparation of L-serine derivatives of the formula:

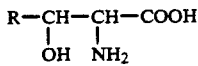

wherein R is an organic residue having at least two carbon atoms by reacting an aldehyde with glycine in aqueous solution at a pH of 5 to 10 and a temperature of 5 to 60° C. in the presence of an enzyme obtained from microorganisms belonging to the genera Escherichia, Citrobacter, Klebsiella, Aerobacter, Serratio, Proteus, Bacillus, Staphylococcus, Arthrobacter, Bacterium, Xanthomonas, Candida, Debaryomyces, Corynebacterium and Brevibacterium. It is suggested that the active enzyme in this reaction is threonine aldolase. In order to improve yields, it is recommended that the amount of glycine in the reaction system be equimolar with or in excess of the aldehyde, and that the amount of aldehyde in the reaction system be limited to from 0.1 to 10% by weight of the reaction mixture.

A similar description of threonine aldolase for the preparation of L-beta-phenylserine is set forth in Japanese patent document SHO 54-3952, published Feb. 28, 1979.

A number of authors have also suggested that glycine may be condensed with formaldehyde to give L-serine using SHMT. See, Hamilton et al., *Trends in Biotechnology*, Vol. 3, No. 1, pages 64-68 (1985); and U.K. Published Patent Application No. 2130216A, filed Nov. 18, 1983).

European Patent Application No. 0 220 923, published May 6, 1987, corresponding to commonly assigned copending U.S. Patent application Ser. No. 789,595, filed Oct. 21, 1985, describes the use of SHMT obtained from a genetically engineered *Escherichia coli* strain transformed with the pGS29 plasmid for condensing benzaldehyde and glycine methyl ester to produce betaphenylserine methyl ester. The reaction conditions employed during the condensation reaction include a pH of from 6.5 to 9, a temperature of from 10 to 65° C., a benzaldehyde concentration of from 10 to 100 mM and a glycine ester from 10 to 150 mM. While at a beta-phenylserine methyl ester yield of 1.48 g/l, this process produced a beta-phenylserine methyl ester product containing as much as 83% erythro isomer, it has been found that as the yield is increased the amount of threo isomer present in the product increases until at commercial rates of production substantial amounts of threo isomer are present.

While the prior art has thus recognized that various enzymes can be employed to catalyze the aldol condensation of glycine and aldehydes to make L-serine derivatives, the processes of the prior art have suffered from a number of disadvantages. The use of excess glycine in the prior art processes has resulted in a L-serine derivative product containing large amounts of residual glycine. The presence of this glycine in the product not only leads to high raw material costs, but in addition, requires the use of a troublesome separation procedure in order to separate the glycine from the L-serine derivative, further adversely effecting the process economics.

Moreover, with the processes of the prior art, it has been found that the L-seine derivative formed comprises a mixture of optical isomers containing predominantly L-threo isomer at equilibrium. While for some purpose such mixtures are satisfactory, other purposes, such as the preparation of aspartame from L-phenylserine, require the use of only the L-erythro isomer of such L-serine derivatives. In end-uses of this latter type, the l-threo isomer is either non-reactive, or leads to contamination of desirable stereoisomers with undesirable stereoisomers.

SUMMARY OF THE INVENTION

In accordance with the present invention, there has been provided a process for the preparation of L-serine derivatives of the formula (I):

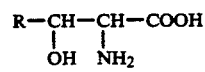

wherein R is hydrogen, or an organic radial containing form about 1 to 25 carbon atoms, which in its broadest aspect comprises the steps of:

(a) reacting an aldehyde of the formula : RCHO(II), wherein R is as set forth above, with glycine in aqueous solution having a pH of from about 7.5 to 10 under result effective reaction conditions in the present of an amount of an enzyme effective to form an aqueous phase containing the L-serine derivative;

(b) extracting the aqueous phase of step (a) with an organic phase comprising an aldehyde of the formula RCHO(II) (which may be the same or different than the aldehyde employed in step (a)), or a mixture of such aldehyde and a water immiscible organic solvent; and (c) extracting the organic phase of step (b) with an aqueous phase having a pH of less than about 7.0 to produce an aqueous L-serine derivative product phase.

The aqueous L-serine derivative product phase produced in step (c) contains very low residual glycine and low aldehyde, and can either be employed as is, or can be treated to recover pure L-serine derivative. In addition to these purity advantages, the claimed process also accrues enhanced yields of the L-serine derivatives. The extraction step of the invention shifts the equilibrium in favor of L-serine derivative production and away from L-serine derivative cleavage such that a greater amount of L-serine derivative product is obtained.

In a particularly preferred embodiment, the foregoing process is adapted to provide for the selective synthesis of the L-erythro isomer of the L-serine derivatives. In accordance with this embodiment, which requires the use of aldehydes wherein R is an organic radical, production of the L-threo isomer is suppressed through the use in step (a) of a set of critical reaction parameters comprising a pH of from about 7.5 to 10, a temperature of less than 60° (and preferably less than 40° C.), a glycine concentration of less than about 500 grams/liter, an aldehyde concentration of less than about 90 grams/liter, and a molar ratio of glycine to aldehyde of from about 4:1 to about 100:1. The resulting L-serine derivative-containing phase is then extracted with organic phase and acidic aqueous phase as set forth above in steps (b) and (c) to produce an aqueous product phase containing primarily L-erythro isomer. For purposes of the present application and appended claims, the phrase "containing primarily L-erythro isomer" means that greater than 50% on a molar basis of the L-serine derivative present in the aqueous product phase comprises the L-erythro isomer. In this embodiment of the invention, preferably at least 75%, and most preferably at least 90% on a molar basis of the L-serine derivative product comprises the L-erythro isomer.

In accordance with the present invention, it has been discovered that through the use of the foregoing preferred form of the invention, erythro/threo ratios of up to 16/1, corresponding to an erythro purity of 94%, can readily be obtained at commercially desirable rates of production. This result is particularly surprising since, as noted above, conventional enzyme catalyzed reactions yield mixtures of erythro and threo isomers containing predominantly threo isomer (approximately 3:1 threo:erythro ratio) at commercial rates of production. The fact that pH can be used to suppress L-threo synthesis is itself surprising since Ulevitch et al., *Biochemistry*, Vol. 16, No. 24, pages 5342-5350 and 5356-5369 (1977) indicate that the pH dependence of the reversible cleavage of the L-erythro and L-threo phenylserine isomers is the same for both isomers.

Other embodiments, features and advantages of the present invention will become apparent to those skilled in the art upon examination of the following detailed description of the invention and accompanying drawings.

DETAILED DESCRIPTION OF THE INVENTION

Figure 1:
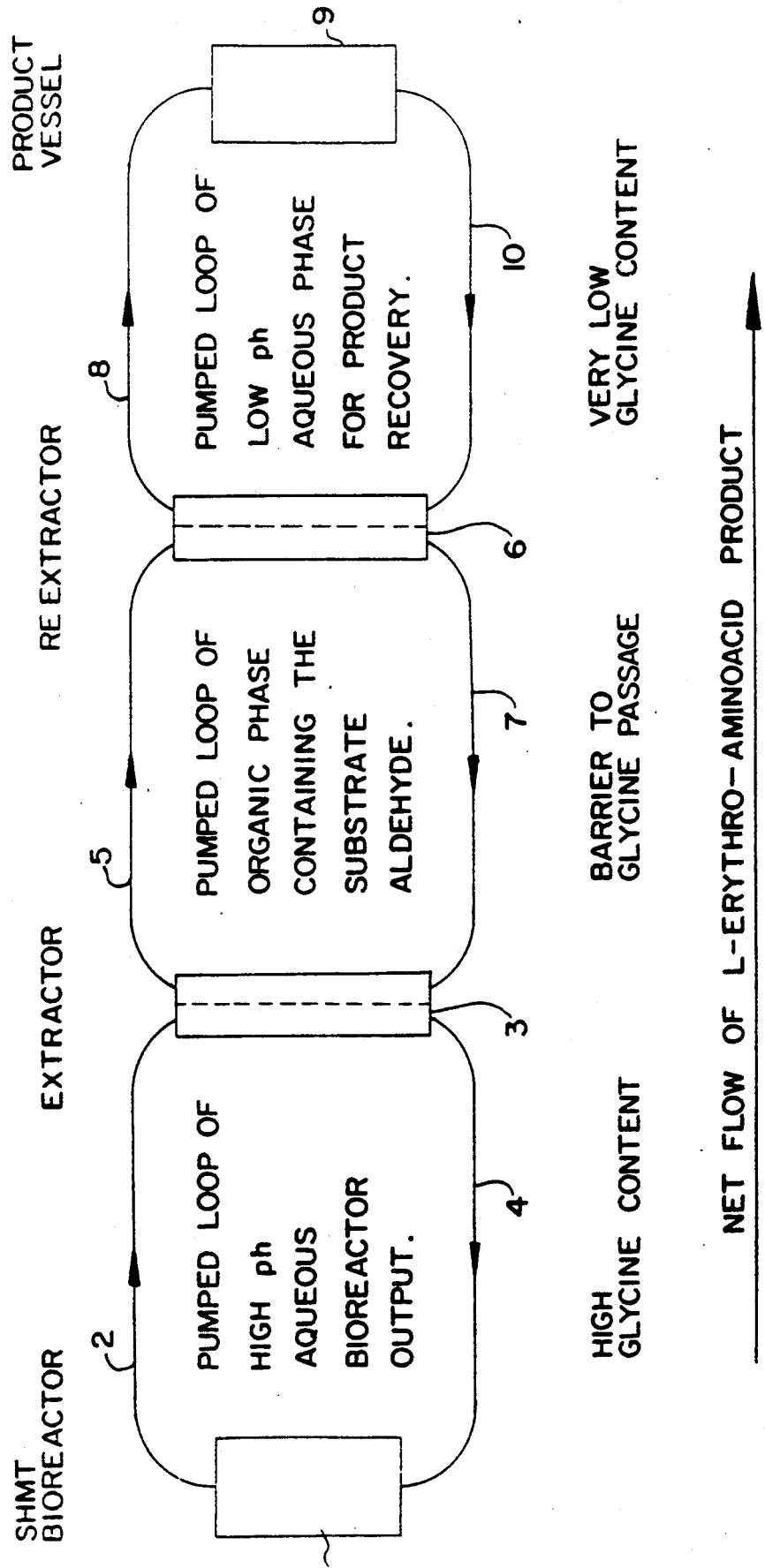
FIG. 1 is a schematic flow diagram of one embodiment of the invention directed to the preferential preparation of L-erythro-phenylserine using a continuous extraction/re-extraction procedure.

In its broadest form, the process of this invention comprises the steps of (a) reacting an aldehyde of the formula (II) above and glycine in the presence of enzyme under result effective reaction conditions to form an L-serine derivative of the formula (I); (b) extracting the resulting product mixture of step (a) with an aldehyde-containing organic phase; and (c) extracting the organic phase of step (b) with an acidic aqueous phase (also referred to herein as the re-extraction step) to produce an aqueous L-serine derivative product phase. Surprisingly, it has been discovered that this process not only enables the recovery of the L-serine derivatives of formula (I) in higher yields and with less glycine contamination than with the conventional enzyme catalyzed processes for the preparation of these compounds, but that this process may be adapted in accordance with the teachings of this invention to achieve the preferential formation of the L-erythro isomers of these compounds.

While not wishing to be bound by any particular theory or mechanism, it has been discovered by the instant inventors that synthesis of the L-threo isomer, relative to the L-erythro isomer, is suppressed at reaction conditions in the range of pH 7.5 to 10. This result is particularly surprising since, as noted above, studies of the reversible cleavage of the L-phenylserines indicated that the response of both the L-erythro and L-threo isomers to changes in pH was similar, suggesting that pH conditions that suppress L-threo isomer formation should also suppress L-erythro isomer formation.

pH, however, is not the only factor responsible for the ability of the process of this invention to selectively prepare the L-erythro isomers of the serine derivatives of ormula I. Other factors such as temperature and concentration of glycine and aldehyde contribute to this result.

Also critical is the use of the extraction/ re-extraction procedure of the invention. Not only does this procedure reduce the amount of residual glycine present in the aqueous L-serine derivative product phase, but the removal of L-serine derivative from the reaction mixture shifts the equilibrium of the reversible L-serine derivative synthesis reaction such that the reverse reaction (the cleavage reaction) is thermodynamically not favored. As a result, higher yields of L-serine derivative are obtained since loss due to cleavage is reduced. Moreover, minimization of the cleavage reaction prevents the L-erythro isomer from reaching its equilibrium with the l-threo isomer such that predominantly wit the L-threo isomer can be obtained in high yield despite an unfavorable equilibrium.

The Aldol Condensation Reaction

Depending upon whether a mixture of L-erythro and L-threo isomers is to be made or whether the L-erythro isomer is to be preferentially synthesized, the reaction conditions can vary over a wide range. The aldol condensation reaction will typically be conducted in an aqueous solution containing enzyme, glycine and aldehyde at a pH of from about 7.5 to 10 (preferably from 8.0 to 10.0), and a temperature ranging from the freezing point of the reaction medium and/or reactants to about 60° C., e.g., from 5 to 60° C. In order to maintain the pH of the reaction system within the desired pH range during the reaction a buffer such as a phosphate, tris, Hepes (N-2-hydroxymethylpiperazine-N'-2-ethane sulfonic acid), Mes (2-(N-morpholino) ethane sulfonic acid),or ammonium chloride-ammonia, etc., buffer may be employed. Preferably, the reaction is conducted with stirring.

The pH of the reaction medium is critical to the successful practice of the process of this invention, whether a diastereoisomeric mixture of L-threo and erythro isomers is to be made or whether the L-erythro isomer is to be preferentially synthesized. While not wishing to be bound by any particular theory or mechanism of action, it is believed that the selective extraction of the L-serine derivative into the organic phase requires the formation of a L-serine derivative/aldehyde Schiff base. The L-serine derivatives themselves (like glycine) have only limited solubility in organic media. In accordance with this invention, however, it has been discovered that upon contact of the aldehyde-containing organic extractant phase with the aqueous reaction medium, wherein the pH is maintained in the range of 7.5 to 10, an aldehyde/L-serine derivative Schiff base is formed which is soluble in and readily extracted into the organic phase. In contrast, glycine has less tendency to form a Schiff base at this pH range, and its Schiff base has much less tendency to be extracted into the organic phase.

Adjustment of the pH may be made by the addition of suitable organic or inorganic acids and bases to the reaction medium. The only limitation on the selection of a suitable acid or base is that the same should not form an insoluble salt with the L-serine derivative Schiff base. Usually pH adjustment will require the addition of a base. For reasons of economy and convenience, the base is typically a basic salt of an alkali metal, for example, the lithium, sodium and potassium hydroxides, carbonates, bicarbonates, etc. Other bases, such as ammonium hydroxide, alkyl substituted ammonium hydroxide, etc., however, may also be conveniently employed.

Although it is less preferred, the aldol condensation reaction may be conducted at a pH below 7.5, e.g., in the range of pH 5.0 to 7.5. In such case, however, the pH of the aqueous reaction media must be adjusted to a pH in the range of 7.5 to 10 prior to organic extraction. Since in the preferred embodiment the aqueous reaction medium is continuously extracted with the organic phase, maintenance of a pH in the range of 5.0 to 7.5 in the reaction medium would require a further pH adjustment following the extraction step to return the pH of the aqueous reaction medium to the pH 5.0 to 7.5 range. Use of a pH below 7.5 would thus require the addition of two pH adjustment steps to the process, and accordingly is not preferred, but may be employed where desired.

The aldehyde and glycine concentrations employed during the reaction may range up to the saturation point for each of these compounds (i.e., up to 1000 grams/liter glycine and up to about 90 grams/liter aldehyde), with the glycine usually being in molar excess relative to the aldehyde. Typically, the concentration of aldehyde will range from about 1 to about 20 grams/liter, with the concentration of glycine ranging from about 10 to about 300 grams/liter. In the preferred embodiment, the glycine concentration comprises about 100 to 200 grams/ liter, e.g., about 150 grams/liter.

Where L-erythro isomer is preferentially desired, it is critical that the pH of the solution be maintained in the range of from about 7.5 to 10, preferably in the range of from about 8.5 to 10, and most preferably from about 9 to 9.5. The reaction temperature employed in this preferred embodiment of the invention is preferably maintained at less than 40° C., e.g., from about 5 to 30° C., and most preferably at from about 10 to 25° C. In order to preferentially obtain the L-erythro isomer, a low concentration of aldehyde is required. In this embodiment, the aldehyde concentration will typically be maintained at less than 90 grams/liter, preferably in the range of from 1 to 10 grams/liter, and most preferably from about 2 to 5 grams/liter. Glycine is employed in a molar excess relative to aldehyde of from about 4:1 to about 100:1, preferably from about 10:1 to about 100:1 and most preferably from about 15 to about 25 moles of glycine per mole of aldehyde, with a concentration from about 10 to about 300 grams/liter. Most preferably, the reaction mixture will contain a glycine concentration of from about 100 to 200 grams/liter, e.g., about 150 grams/liter.

Useful aldehydes of the formula (II) include aldehydes wherein the R group is alkyl, alkenyl or alkynl of from 1 to 25 carbon atoms, preferably 1 to 15 carbon atoms and most preferably 1 to 10 carbon atoms; aryl of 6 to 10 carbon atoms; alkaryl of 1 to 25 carbon atoms; aryl substituted with hydroxy, nitro, amine or halide groups; heterocyclic aldehydes, and various other aldehydes such as salicylaldehyde; cinnamaldehyde; formal carboxylic acids such as formylacetic acid; ketoaldehydes such as glyoxal, methyl glyoxal, phenylglyoxal, etc.; succinaldehyde, acrylaldehyde, crotonaldehyde, propiolaldehyde, trichloroacetaldehyde; vanillin; as well as p-methylsulfonylaldehyde, etc. Specific examples of a wide variety of useful aldehydes are set forth in U.S. Pat. No. 3,871,958, the entirety of which is herein incorporated by reference and relied on in its entirety. Particularly preferred aldehydes for use in the process of this invention include benzaldehyde; hydroxysubstituted benzaldehydes, such as 3,4- and 2,4-dihydroxybenzaldehyde; and acetaldehyde.

The enzyme employed in this invention may comprise any of the enzymes known in the art to catalyze the aldol condensation of glycine and aldehydes. Such enzymes are generally referred to in the literature as serine hydroxymethyltransferase (SHMT), but in addition have also been referred to as threonine aldolase, serine hydroxymethylase, and allothreonine aldolase. While minor variations exist in these enzymes depending on their source, all of the enzymes of this class appear to possess similar reaction mechanisms and active site structures and are useful in the process of this invention and are intended to be encompassed thereby. For the sake of uniformity of nomenclature, therefore, for the purposes of this invention, all of the enzymes which are capable of catalyzing the glycine-aldehyde condensation reaction will be referred to as serine hydroxymethyltransferases (SHMT). As used herein, the terms "serine hydroxymethyltransferase" and "SHMT" are thus defined to include all of the various enzymes which catalyze the condensation of glycine and aldehyde to L-serine derivatives of formula (I).

As noted above, SHMT is readily available, and may be obtained from various mammalian liver extracts by art recognized techniques. In addition, this enzyme may be obtained from any of the various microorganisms described in U.S. Pat. No. 3,871,958, the entirety of which is incorporated by reference and relied on in its entirety.

In the preferred embodiment, genetically engineered microorganisms transformed with high-copy-number plasmids containing the *E. coli glyA* gene are used as the enzyme source. The glyA gene is contained in a 3.3 kilobase Sal I-EcoRI fragment. One known plasmid, designated pGS29, is formed by insertion of the glyA gene into the tetracycline resistance gene of pBR322. *E. coli* strains transformed with the pGS29 plasmid produce as much as 26 times the amount of SHMT, as compared with wild-type strains. Further details concerning the preparation of such *E. coli* strains are set forth in Schirch et al., *J. Bacteriology*, Vol. 163, No. 1, pages 1–7 (1985) and Plamann et al., *Nucleic Acids Research*, Vol. 11, No. 7, pages 2065–2075 (1983).

A genetically engineered *Klebsiella aerogenes* strain, stabilized by nutritional selection, is reported by Hamilton et al. in *Trends in Biochemistry*, Vol. 3, No. 1, pages 64–68 (1985). This strain was prepared by insertion of the *E. coli glyA* gene into the tetracycline resistance gene of pBR322. The resulting plasmid, designated pGX122, was subcloned into a plasmid with multiple restriction endonuclease sites (pGX 145) to create the plasmid pGX139. A trp operon stabilized glyA plasmid was next prepared by insertion of the glyA gene from pBX139 into the trp operon plasmid pGX110 to create the plasmid pGX2236, which was inserted into *K. aerogenes* GX1705, a strain containing a mutation in the tryptophan synthetase gene. As a result of this mutation, only cells that retained the plasmid are capable of growing in media lacking tryptophan.

Techniques for culturing SHMT containing microorganisms are well known to those skilled in the art, and are described, for example, in U.S. Pat. No. 3,871,958, the entirety of which is herein incorporated by reference and relied on in its entirety.

The enzyme source may comprise intact, whole cells, an aqueous suspension of ground cells, a filtrate of such suspensions, crude extracts of such cells, or the pure enzyme. Techniques for the recovery and purification of SHMT from liver and bacterial cells are well known to those skilled in the art, and are described for example in Ulevitch et al., *Biochemistry*, Vol. 16, No. 24, pages 5342–5350 (1977); and in Schirch et al., *J. Bacteriology*, Vol. 163, No. 1, pages 1–7 (1985)

The amount of enzyme present during the reaction can vary over a wide range. Typically, the enzyme will be used in an amount of from about 100 to 4,000,000 units/ liter, preferably from about 1000 to about 1,000,000 units/liter, and most preferably from about 5,000 to 500,000 units/liter. As used herein a unit of SHMT is equal to that amount of enzyme which catalyzes production of 1 micromole of benzaldehyde per minute from L-threophenylserine at 25° C., neutral pH.

The reaction may be conducted by culturing a suitable SHMT microorganism source in a conventional nutrient medium containing glycine and aldehyde. Generally, however, the reaction is conducted by adding SHMT to an aqueous solution containing glycine and aldehyde. The reaction may be conducted on a batch basis or on a continuous basis by the intermittent or continuous addition of glycine and aldehyde. SHMT requires pyridoxal-5-phosphate (P-5-P) for activity. Where the reaction is conducted in the microorganism culture medium, addition of P-5-P is not required, since the microorganism is able to synthesize in vivo the P-5-P necessary for SHMT activity. In all other cases P-5-P must be added to the reaction mixture for SHMT activity. Typically, P-5-P will be employed in an amount equimolar to, or smaller than, the amount of enzyme present. Use of amounts of P-5-P greater than equimolar quantities are not preferred since the use of excess P-5-P leads to non-enzymatic synthesis and a racemic product mixture. Preferably the amount of P-5-P employed will be an amount sufficient to activate the SHMT enzyme not exceeding an equimolar amount. Where whole cells are used as the enzyme source, pyridoxine or pyridoxal may replace P-5-P. These compounds are converted in vivo by the microorganism to P-5-P.

When L-serine is to be produced by the process of the invention, tetrahydrofolate (THF) or similar folic acid derivatives are required to enhance activity in the bioreactor. The use of such folate compounds may also be desirable during the production of derivatives of L-serine in order to enhance total L-serine derivative synthesis.

The SHMT enzyme may be immobilized, if desired, using any of a variety of supports and immobilization techniques well known to those skilled in the art. Where non-immobilized enzyme is employed, in the preferred embodiment the SHMT enzyme is preferably separated from the reaction mixture by a suitable separation technique. such as dialysis, ultrafiltration, etc., prior to extraction of the L-serine derivative-containing reaction mixture with the organic phase. This expedient is desirable in order to prevent the L-erythro isomer from coming into equilibrium with tis L-threo isomer via the SHMT catalyzed cleavage and re-condensation of the same into the thermodynamically more favored L-threo isomer. Moreover, contact between the enzyme and organic phase has a deleterious effect on enzyme stability and on phase separation.

The Extraction/Re-extraction Procedure

The organic phase used to extract the L-serine derivative reaction mixture may comprise (i) an aldehyde of formula (II), which may be the same or different than the aldehyde employed in the condensation reaction, or alternatively may comprise mixtures of aldehyde and one or more water immisicible solvents. As used herein, the term "water-immisicible solvent" means that the solvent forms a two-phase system with water. Such solvents are well known to those skilled int he art; and include, by way of example, the alkyl ester of carboxylic acids such as ethyl acetate, isopropyl acetate, butyl acetate, and isobutyl acetate; lower alkyl halides such as chloroform or ethylene dichloride; detones such as methylisobutyl ketone; aromatic hydrocarbons such as benzene, toluene, or mixtures thereof; higher alcohols such as t-butanol, cyclohexanol and benxyl alcohol; and various other solvents such as butanediol, triethylene glycol, dioxane, isopropyl ether, trichloroethylene, tetrachloroethylene and the like.

The presence of aldehyde int he organic phase is a critical feature of the process of this invention and is essential to the successful extraction of the L-serine derivative into the organic phase. As noted above, in the absence of aldehyde the L-serine derivative has only limited solubility in the organic phase. While not wishing to be bound by any particular theory or mechanism of action, it is believed that the aldehyde reacts with the L-serine derivative to form the Schiff base of such compound. The Schiff base is preferentially soluble in organic media and accordingly can be readily extracted into the same from the aqueous reaction media.

For successful practice of the invention process, therefore, the aldehyde must be present in the organic phase in an amount at least sufficient to convert the L-serine derivative present in the aqueous reaction media to its Schiff base. Typically, the organic phase will contain from about 5 to 100% by volume of aldehyde, preferably from about 5 to 50% by volume of aldehyde, and most preferably from about 10 to 35% by volume of aldehyde.

Following extraction into the organic phase, the L-serine derivative is then contacted with an aqueous phase having a pH of less than 7.0, preferably less than 6.0, and most preferably less than 5.0, to form the aqueous L-serine derivative. The pH of the aqueous phase is also critical to the successful operation of the invention. At a pH of less than 7.0, the L-serine derivative/aldehyde Schiff base will be broken such that the free L-serine derivative is preferentially extracted into the aqueous phase.

The extraction/re-extraction procedure is conducted such that build-up of L-serine derivative in the reactor is prevented. While this objective may be achieved by intermittent extractions of adequate frequency, it is preferred that the L-serine derivative be removed from the reaction media continuously as it is synthesized by continuous extraction/re-extraction. For the preferential synthesis of L-erythro isomer, the rate of extraction of the L-erythro isomer must be greater than one-half the rate of total L-serine derivative production in the bioreactor, and most preferably approximately equal to or greater than the rate of L-serine derivative production in the bioreactor. Such rates of extraction can readily be achieved by those skilled in the art by appropriate balancing of flow rates, ratios of flow rates, ratios of volumes of extractants and aqueous reaction medium, contact times, equipment sizes, etc. The extraction and re-extraction steps may be conducted in concurrent fashion, but are preferably conducted countercurrently.

Figure 2:
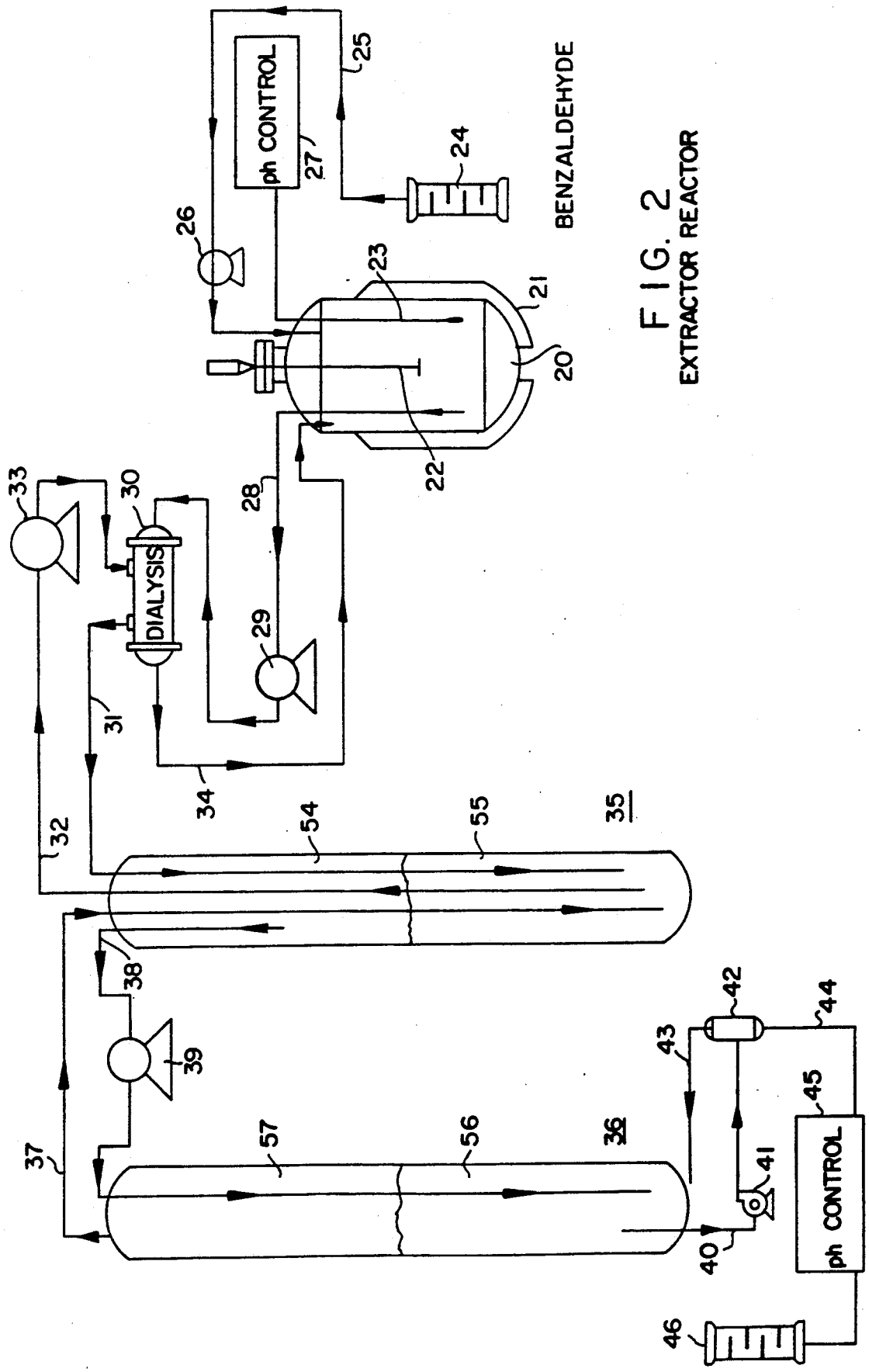
FIG. 2 is a schematic flow diagram of the apparatus employed in conducting Example 7 infra.

FIG. 1 is a schematic flow diagram of a preferred method for conducting the process of the invention which employs a continuous, countercurrent extraction/re-extraction procedure. In the bioreactor 1, SHMT, glycine, aldehyde and P-5-P are reacted in aqueous solution under conditions described above to form the L-serine derivative. A portion of the aqueous reaction mixture is continuously removed through line 2 for countercurrent extraction with organic phase in extractor vessel 3. Where non-immobilized enzyme is employed, an ultrafilter or dialysis device is preferably interposed prior to the extractor vessel 3 for enzyme separation, such as is illustrated in FIG. 2 to be discussed hereinafter. In the extractor vessel 3, the L-serine derivative forms an aldehyde/L-serine derivative Schiff base which is extracted into the organic extractant phase. The L-serine derivative depleted aqueous reaction mixture, high in glycine content, is continuously returned to the reactor 1 through line 4.

The organic phase, in turn, is continuously recirculated via lines 5 and 7 through re-extractor vessel 6 where it is countercurrently contacted with a low pH aqueous phase, which is itself continuously recirculated from product vessel 9 via lines 8 and 10. As discussed above, in the re-extractor vessel 6 the aldehyde/L-serine derivative Schiff base is broken, resulting in the re-extraction of the L-serine derivative into aqueous solution. The L-serine derivative containing aqueous solution is collected in product vessel 9, and may be either used as is, or processed using known techniques such as, for example, precipitation, chromatography, ion exchange, etc., to recover pure L-serine derivative.

The L-serine derivatives produced by the process of this invention are valuable intermediates for the production of compounds such as epinephrine, norepinephrine, aspartame and various other dipeptides, chloramphenicol, as well as various pharmaceuticals.

The following Examples serve to give specific illustration of the practice of this invention, but they are not intended in any way to act to limit the scope of this invention.

In each of the examples set forth hereinafter, the SHMT enzyme source comprised a genetically engineered $E.$ $coli$ strain which was transformed by conventional procedures to contain the plasmid pGS29. This strain, identified by the assignee hereof as GR64/pGS29, will have been deposited with the American Type Culture Collection, 12301 Parklawn Drive, Rockville, Maryland 20852, ATCC Deposit No. 67673, with no restrictions as to availability, and W. R. Grace & Co., the assignee hereof, assures permanent availability of the culture to the public through ATCC upon the grant hereof.

While as noted above, the process of this invention contemplates the use of whole cells, extracts, etc., as SHMT enzyme sources, in the Examples which follow SHMT obtained by fermentation of the aforementioned GR64/pGS29 $E.$ $coli$ strain and purified to homogeneity was employed. The GR64/pGS29 $E.$ $coli$ strain was cultured as follows: One liter of seed culture was first prepared by aseptically inoculating a sterilized (121° C. for 25 minutes) two liter shake flask containing one liter of an aqueous culture medium comprising 60.0 grams of tryptocase soy broth (Difco Laboratories, Inc., Detroit, Michigan), 15.0 grams of $K_2HPO_4$, and four drops of P-2000 silicone antifoam (Dow Chemical Company, Midlands, Michigan) with an ampoule of microorganism thawed under tap water (which was previously stored at $-70°$ C.). Prior to inoculation, the pH of the culture medium was adjusted to pH 7.2 to 7.5 by the addition of 1.3 ml of concentrated $H_2SO_4$. This mixture was then incubated at 31° C. for 8 to 10 hours at 250 rpm.

This seed culture was then added to a sterilized (121° C., 30 minutes) 20 liter fermentation vessel containing 13.0 liters of an aqueous culture medium comprising 220 ml of separately sterilized, 63% glucose solution, 322 grams of casein protein digest (NZ Amine A, Schofield Products, Norwich, New York), 112 grams of Amberex 1003 yeast extract (Universal Foods, Hackensack, N.J.), 56 grams of $(NH_4)_2SO_4$, 14 grams of $MgSO_4.7H_2O$, 70 grams of $KH_2PO_4$, 220 ml of a trace mineral solution (containing 8.8 grams/liter of $ZnSO_4.7H_2O$, 10 grams/liter $FeSO_4.7H_2O$, 0.06 grams/liter $CuSO_4.5H_2O$, 0.12 grams/liter of $CoCl_2.6H_2O$, 0.055 grams/liter of $CaCl_2.2H_2O$, .088 grams/liter of $Na_2B_4O_7.10H_2O$, 0.053 grams/liter $Na_2Mo_2O_4.2H_2O$, and 7.5 grams/liter of $MnSO_4.H_2O$ in 6 N $NH_4OH$), and 1.4 ml of P-2000 silicone antifoam (Dow Chemical Company, Midlands, Michigan) to produce 14.0 liters of fermentation medium.

Prior to addition of the seed culture, the pH of the medium was adjusted to pH 7.0 by the addition of 17 ml of 50% NaOH. Fermentation thereafter proceeded over a period of about 18 hours at pH 7.0 (controlled via addition of 6N $NH_4OH$), a temperature of 30° C., an airflow of 14 slpm, and 1200 rpms until the optical density at 640 nm of the medium reached 9.0. During the fermentation period, the medium was sampled every two hours for pH, optical density and glucose. The dissolved oxygen during the fermentation period was found to fall below 15%. Upon the attainment of an optical density of 9.0, the bacteria were harvested, and the SHMT enzyme purified to homogeneity according to the procedure of Schirch et al., *Journal of Bacteriology*, Vol. 163, No. 1, pages 1-7 (1985) reported at page 3 thereof, omitting, however, the hydroxylapatite and TSK 3000 HPLC treatments.

Unless noted otherwise, in the Examples which follow, L-erythro and L-threo phenylserine were monitored by reverse phase high performance liquid chromatography using a Supercosil C-18 column (Supelco, Inc., Bellefonte, Pennsylvania), Shimadzu LC-4A HPLC, SPD 2AS U.V. detector, Sil-2AS autosampler and CR3A integrator, and as elutants aqueous phosphate buffer (prepared from HPLC grade ultra-pure water) and HPLC grade acetonitrile. Wavelength detection was at 220 nm. 2.0 grams/liter of L-erythro and L-threo phenylserine in HPLC grade methanol, and 3:4, 1:2, 1:4 and 1:10 dilutions thereof were used as standards. Samples were typically diluted 1:15 in HPLC grade methanol to adjust the concentrations within the range of the standards.

EXAMPLE 1

This example demonstrates the effect of benzaldehyde concentration on the relative rates of L-erythro and L-threo-phenylserine synthesis. $50 \times 10^{-6}$M pyridoxal-5-phosphate, 4,000 units/liter of purified SHMT, 88 grams/liter glycine, and an amount of benzaldehyde as indicated in Table I below in 0.05 M HEPES (N-2-hydroxyethylpiperazine-N'-ethane sulfonic acid) buffer at pH 7.0 were reacted at 25° C. in a 50-ml. glass round bottom flask equipped with an agitator and heated with a temperature controlled bath. Samples of the reaction mixture were taken and analyzed hourly for L-erythro and L-threophenylserine concentration. The results of this experiment are set forth below.

TABLE I

| Benzaldehyde (grams/liter) | 0.106 | 0.21 | 0.33 |
|---|---|---|---|
| Rate of L-erythro phenylserine synthesis (grams/liter/hour) | 0.405 | 0.78 | 1.04 |
| Rate of L-threo phenylserine synthesis (grams/liter/hour) | 0.013 | 0.054 | 0.10 |

As can be seen from Table I, the rate of L-erythro-phenylserine synthesis is proportional to benzaldehyde concentration while the rate of L-threo-phenylserine synthesis appears proportional to the square of benzaldehyde concentration. This result indicates that the preferential formation of the L-erythro-isomer of phenylserine is enhanced by the use of low concentrations of aldehyde.

EXAMPLE 2

This example demonstrates the effect of pH on L-erythro-/L-threo-phenylserine synthesis. A saturating concentration of $^{13}$C labelled benzaldehyde (5.6 grams/liter), and 1.8 M (158 grams/liter) glycine were reacted at 25° C. for 12 hours at pH 7.6 and pH 9.6 in 0.7 ml NMR tubes. The reaction mixture at pH 7.6 contained 0.05 M HEPES buffer. The pH 9.6 reaction was self-buffered by the 1.8 M (158 grams/liter) glycine. Both reactions were started by adding a concentrated solution of purified SHMT (70,000 units/liter of SHMT in pH 8 Tris buffer) until the final concentration of enzyme in the reaction mixture was 1,000 units/liter SHMT. During this period, each solution was analyzed every 0.5 hours for L-erythro and L-threo-phenylserine production by $^{13}$C-NMR. The results are reported in Table II.

TABLE II

| pH | 7.6 | 9.6 |
|---|---|---|
| Rate of L-erythro-phenylserine synthesis (grams/liter/hour) | 0.6 | 0.3 |
| Rate of L-threo-phenylserine synthesis (grams/liter/hour) | 0.1 | 0.01 |

As can be seen from the above data, at pH 9.6, the rate of L-erythro isomer synthesis is about ½ that at pH 7.6. In contrast, the rate of L-threo isomer synthesis at pH 9.6 is only 1/10 that at pH 7.6, and approximately 1/30 the rate of L-erythro isomer production at this pH.

EXAMPLE 3

This example demonstrates the criticality of the presence of aldehyde in the organic extractant phase. In this experiment, 1 ml of an aqueous solution containing 1.5 M glycine (132 grams/liter), pH 9.1 (adjusted with KOH), and 0.05 M D,L-threo-phenylserine (purchased commercially from Sigma Chemical, St. Louis, Missouri), corresponding to 9 grams/liter, was extracted with 5 ml of the organic solvents indicated in Table III below. The amino acids in the organic phase (after extraction) were determined by HPLC. The percentage of amino acid extracted is presented in Table III.

TABLE III

| Solvent Composition | % Glycine | % phenylserine |
|---|---|---|
| Ethyl Acetate/butanol (4:1) | <1% | 1.5% |
| Ethyl acetate/butanol/benzaldehyde (3:1:1) | <1% | 15% |
| Ethyl Acetate/butanol/benzaldehyde (2:1:2) | <1% | 25% |
| Ethyl Acetate/benzyl alcohol (4:1) | <1% | <1% |
| Ethyl Acetate/benzyl alcohol/benzaldehyde (3:1:1) | <1% | 15% |

As can be seen from Table III, solvent media lacking aldehyde were unable to effectively extract phenylserine from the aqueous reaction media.

EXAMPLE 4

This example demonstrates the effect of pH on the extraction of phenylserine from aqueous media. In this example, 1 ml samples of a series of aqueous solutions containing 1.5M (132 grams/liter) glycine and 0.05M phenylserine (the commercially purchased D,L-threo phenylserine of Example 3), corresponding to 9 grams/liter of phenylserine, with the pH adjusted with KOH as indicated in Table IV below, were extracted with an ethyl acetate/benzyl alcohol/benzaldehyde (3:1:1) organic solvent mixture. Following extraction, the organic phase was analyzed for % glycine and % phenylserine extracted by HPLC. The percentage of amino acid extracted at each pH used is set forth in Table IV.

TABLE IV

| pH | % Glycine | % Phenylserine |
|---|---|---|
| 7.6 | <1% | 4% |
| 8.6 | <1% | 6% |
| 9.2 | <1% | 15% |
| 9.6 | <1% | 18% |

Taken together, the data in Table III and IV indicate that with the organic extractants used in the process of this invention, it is possible to preferentially extract phenylserine from glycine under the same conditions of pH which suppress production of L-threo-phenylserine and favor production of L-erythrophenylserine by SHMT.

EXAMPLE 5

This example demonstrates the effect of temperature on the relative rates of L-erythro- and L-threophenylserine synthesis. To a one-liter glass round bottom flask equipped with an agitator and heated with a temperature controlled bath, one liter of reaction solution containing 175 grams/liter glycine at pH 8 and 4000 units/liter of SHMT were added and brought to the reaction temperatures indicated in Table V. Benzaldehyde was then added to the agitated solution at a rate of 16 grams/liter/hour. Samples were taken periodically to monitor the ratio of the isomers and their concentrations. Table V below presents the results of these experiments and shows that lower temperatures favor the production of L-erythro-phenylserine, and that at such lower temperatures a higher ratio of L-erythro- to L-threo-phenylserine can be achieved at high L-erythro-phenylserine concentrations.

TABLE V

Effect of Temperature on the Ratio of Erythro to Threo-Phenylserine

| Temperature °C. | 3 g/L | 5 g/L | 7 g/L | 10 g/L | 15 g/L |
|---|---|---|---|---|---|
| 5 | 15 | 9 | 7 | 6 | 5 |
| 10 | 10 | 7 | 5 | 4 | 3 |
| 35 | 7 | 5 | 3 | 2 | — |
| 45 | 4 | 2 | 1 | 0.8 | — |

EXAMPLE 6

Following the procedure of Example 5, batch reactions (no solvent extraction) were run at a temperature of 10° C., an SHMT concentration of 10,000 units/liter, 175 grams/liter of glycine and a benzaldehyde feed rate of 15 grams/liter/hour until the concentration of L-erythro-phenylserine in the reaction mixture reached 16 grams/liter. As indicated in Table VI below, the pH in each of these reactions was varied from 7 to 9.5 in order to determine the effect of pH on the L-erythro/L-threo ratio at high rates of production (i.e., at a rate of L-erythro-phenylserine production of 16 grams/liter/hour).

TABLE VI

| | pH | | | | |
|---|---|---|---|---|---|
| | 7 | 8 | 8.7 | 9.1 | 9.5 |
| Ratio of L-erythro-to L-threo-phenylserine | 0.5 | 2.3 | 5.6 | 8.9 | 10.1 |

The data in Table VI indicate that at commercial rates of production, pH strongly influences the ratio of L-erythro to L-threo isomer, and that for the preferential formation of L-erythro-phenylserine, the pH of the reaction should be within the range of from about 7.5 to 10, preferably from about 8.5 to 10, and most preferably from about 9 to 9.5.

EXAMPLE 7

This example illustrates a process for the preferential preparation of L-erythro-phenylserine using a continuous, countercurrent extraction procedure in accordance with this invention. The apparatus used in conducting this example is illustrated in FIG. 2. This apparatus comprises a one liter, glass round-bottom flask 20, equipped with a temperature control jacket 21, agitator 22, pH control 27 (Chem Cadet Model R-5984); a hollow fiber dialysis module 30 (Enka C-10 1.1 m² hollow fiber dialysis unit); two 1½ inch inner diameter, three foot long glass columns 35 and 36 equipped with Teflon stoppers on each end; Masterflex pumps 26, 29, 33, 39 and 41; a 100 ml glass mixing vessel 42; a benzaldehyde source 24; an acid source 46; and pH control 45.

In operation, glycine and benzaldehyde, continuously fed via line 25 and pump 26 from benzaldehyde source 24, were condensed in the reactor 20 in the presence of SHMT enzyme. The pH of the reaction mixture was continuously monitored by pH control 27 and electrode 23. A portion of the reaction mixture was continuously removed via line 28 and pump 29 to the dialysis unit 30 wherein enzyme was separated from the reaction mixture and returned to the reactor 20 via line 34. The phenylserine containing ultrafiltrate was circulated through the extraction column 35 by the pump 33 via lines 31 and 32.

In the extraction column 35, the phenylserine containing ultrafiltrate was contacted with an aldehydecontaining organic phase using a countercurrent flow to extract the phenylserine product into the organic phase. The organic extractant phase used in this example comprised a 2:2:1 by volume mixture of 1-butanol, propylacetate and benzaldehyde. The organic phase formed an upper layer identified as 54 in FIG. 2, with the aqueous ultrafiltrate phase forming lower layer 55. Countercurrent extraction was achieved by feeding the organic phase into the lower aqueous phase 55 through line 37, and withdrawing it through the upper organic phase 54 via line 38 and pump 39 so that the organic phase continuously migrated through extraction column 35 from bottom to top.

Organic phase removed from the extraction column 35 via line 38 and pump 39 was then introduced on a continuous basis into the bottom of extraction column 36 where it contacted acidic aqueous phase 56 which extracted the phenylserine from the organic phase. In this example, the acidic aqueous phase comprised an aqueous sulfuric acid solution having a pH of 4. The organic phase formed an upper organic layer 57 in the extraction column 36, and was recirculated via line 37 to extraction column 35, thereby providing a flow of organic phase which was countercurrent to the aqueous phase 56.

For pH control in the extraction column 36, a portion of the aqueous phase 56 was continuously circulated to the mixing vessel 42 via lines 40 and 43 and pump 41. As required, acidic solution (aqueous sulfuric acid, one molar) was fed from supply 46 and pH control 45 through line 44 to the mixing vessel 42.

TABLE VII

| Time (hr) | REACTOR g/L | | | | | PRODUCT g/L | | | | |
|---|---|---|---|---|---|---|---|---|---|---|
| | Glycine | Erythro | Threo | Benz(a) | Ratio(b) | Glycine | Erythro | Threo | Benz(a) | Ratio(b) |
| 1 | 144 | 2.6 | 0.2 | 3 | 13 | 0 ND | 0 | 0 | 4 | |
| 3 | 132 | 4.0 | 0.3 | 4 | 13 | 0 ND | 0.5 | 0.1 | 4 | 5 |
| 6 | 127 | 6.1 | 0.5 | 5 | 12 | 0 ND | 3.3 | 0.3 | 4 | 11 |
| 9 | 124 | 8.6 | 0.9 | 4 | 10 | 0 ND | 5.2 | 0.3 | — | 17 |
| 12 | 118 | 7.3 | 0.8 | 5 | 9 | 0 ND | 8.3 | 0.6 | — | 14 |
| 18 | 106 | 8.2 | 0.6 | 4 | 14 | 0 ND | 10.4 | 1.0 | — | 10 |
| 27 | 83 | 9.6 | 0.7 | 3 | 14 | 0 ND | 16.3 | 1.3 | 4 | 13 |
| 36 | 79 | 11.6 | 1.2 | 4 | 10 | 0 ND | 21.2 | 1.3 | 3 | 16 |

Footnote
(a) Benz = Benzaldehyde
(b) Ratio of L-erthro-phenylserine/L-threo-phenylserine
ND — not detectable, <5 g/L The specific reaction conditions employed in this example were as follows:

(a) bioreactor: pH 9.4 (adjusted with NaOH), temperature 10° C., a SHMT concentration of 10,000 units/liter, a glycine concentration of 144 grams/liter, a benzaldehyde concentration of 3.4 grams/liter, and a pyridoxal-5-phosphate concentration of $1 \times 10^{-5}$ M.

(b) organic phase: 2:2:1 1-butanol/propyl acetate/benzaldehyde mixture.

(c) acidic aqueous phase: aqueous sulfuric acid, pH 4.

Upon start-up, the concentration of total phenylserine in the reactor increased to about 6.7 grams/liter in the first 6 hours, corresponding to a rate of about 1 gram/liter/hour, and then operated at near steady state for close to 30 hours. Under steady state conditions, the ultrafiltrate present as layer 55 in extraction column 35 contained about 144 grams/liter glycine and a saturating amount of benzaldehyde.

In the aqueous product phase 56 the phenylserine concentration increased at a a constant rate of about 1.9 grams/liter/hour, indicating that the extraction procedure was able to match the rate of product synthesis. A final concentration of L-erythrophenylserine of over 21 grams/liter, with an erythro to threo ratio of 16/1, was obtained after 36 hours of operation in the aqueous product phase 56. In contrast, the final concentration of L-erythro-phenylserine in the reactor 20 was approximately 12 grams/liter. The higher concentration of L-erythro-phenylserine in the aqueous product phase 56 as compared with that in the reactor 20 demonstrates the salutary effect of the extraction procedure of this invention on product yield. The results of this example should also be compared with the results obtained without the invention extraction procedure. Absent the use of the invention extraction procedure, even when the SHMT reaction is optimized in accordance with the instant teachings for L-erythrophenylserine production, the best erythro/threo ratio that can be obtained at 20 grams/liter L-erythrophenylserine production is 3/1.

Further details concerning the results of this experiment are set forth in Table VII. As can be seen from this data, the process of this invention shows several advantages over conventional processes. Since the reactants are continuously removed from solution, both the ratio of the erythro to threo isomer in the product and the obtainable phenylserine concentration can be improved over batch reactions. Erythro/threo ratios of up to 16/1 (94% erythro) were obtained with this process at erythro concentrations as high as 21 g/L in the aqueous product phase 56. Furthermore, the aqueous product phase contains very low glycine and is also lower in benzaldehyde than expected for an aqueous solution saturated with neat benzaldehyde.

What is claimed is:

1. A continuous process for the preparation of L-serine derivatives of the formula:

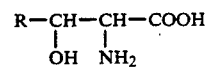

wherein R is hydrogen or an organic radical containing from about 1 to 25 carbon atoms, comprising the steps of:

(a) reacting in a bioreactor an aldehyde of the formula RCHO, wherein R is as set forth above, with glycine in an aqueous solution having a pH of from about 7.5 to about 10 containing an effective amount of an enzyme capable of catalysing a glycine-aldehyde condensation reaction and an additional amount of pyridoxal-5-phosphate co-factor effective to activate the enzyme, and under reaction conditions of temperature and concentration of glycine and aldehyde effective, to form an aqueous phase containing said L-serine derivative;

(b) transferring a portion of the aqueous L-serine-derivative-containing phase of step (a) into an extraction vessel and extracting with an organic phase comprising (i) an aldehyde of the formula RCHO, wherein R is as set forth above, which may be the same or different than the aldehyde employed in step (a) in an amount effective to extract said L-serine derivative into said organic phase, or (ii) a mixture of said aldehyde and a water immisicible organic solvent containing an amount of said aldehyde effective to extract said L-serine derivative into said organic phase;

(c) returning a portion of the aqueous phase of step (b) to said bioreactor;

(d) transferring a portion of the organic phase of step (b) into a reextraction vessel and extracting with an aqueous phase having a pH of less than about 7.0 to produce an aqueous solution containing said L-serine derivative;

(e) returning a portion of the organic phase of step (d) to said extraction vessel; and (f) transferring a portion of the aqueous phase of step (d) containing said L-serine derivative to a product vessel, wherein steps (a) through (f) are conducted continuously.

2. The process of claim 1, wherein the extractions of steps (b) and (d) are conducted with countercurrent contact of the respective aqueous and organic phases.

3. The process of claim 1, wherein the rates of extraction for steps (b) and (d) are greater than one-half the rate of total L-serine derivative synthesis in step (a).

4. The process of claim 3, wherein the concentration of glycine in step (a) is from about 10 to about 300 grams/liter, the concentration of aldehyde is from about 1 to about 20 grams/liter, and a molar excess of glycine relative to aldehyde is present; the pH of the aqueous solution is from about 8.0 to about 10.0; the temperature is from about 5 to 60° C.; the enzyme is present in an amount of from about 1,000 to about 1,000,000 units/liter; and pyridoxal-5-phosphate is present in an amount about equimolar to said enzyme.

5. The process of claim 4 further comprising the step of removing enzyme from the aqueous phase of step (a) prior to organic extraction in step (b).

6. The process of claim 5, wherein the organic phase of step (b) comprises a mixture of said organic solvent and from about 5 to 50% by volume of said aldehyde.

7. The process of claim 6, wherein said organic phase comprises a mixture of said aldehyde and a lower alkyl ester of a lower carboxylic acid or a mixture of said aldehyde, said lower alkyl ester of said lower carboxylic acid and an alcohol.

8. The process of claim 7, wherein said organic phase comprises (iii) a mixture of aldehyde and an ethyl, isopropyl butyl or isobutyl acetate, or (iv) mixtures of (iii) with butanol or benzyl alcohol.

9. The process of claims 4 or 5, wherein the pH of the aqueous phase of step (d) is less than about 5.0.

10. The process of claims 4 or 5, wherein the enzyme is serine hydroxymethyltransferase.

11. The process of claim 10, wherein said serine hydroxymethyltransferase is obtained from a genetically engineered microorganism containing a plasmid having inserted therein the *Escherichia coli glyA* gene.

12. The process of claim 4, wherein the aldehyde is benzaldehyde and said L-serine derivative is L-phenylserine.

13. The process of claim 11, wherein the aldehyde is benzaldehyde and said L-serine derivative is L-phenylserine.

14. A continuous process for the preferential preparation of L-erythro isomer serine derivatives of the formula:

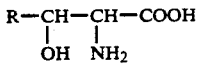

wherein R is an organic radical containing from 1 to 25 carbon atoms, comprising the steps of:
(a) reacting an aldehyde of the formula RCHO, wherein R is as set forth above with glycine in an aqueous solution having a pH of from about 7.5 to about 10, a temperature of from about 5 to 60° C.; an aldehyde concentration of from bout 1 to about 90 grams/liter, a glycine concentration of from about 10 to about 300 grams/ liter, and a molar ratio of glycine to aldehyde of from about 4:1 to about 100:1, in the presence of an effective amount of an enzyme capable of catalyzing a glycine-aldehyde condensation reaction and an additional amount of pyridoxal-5-phosphate effective to activate the enzyme to form an aqueous phase containing the L-erythro isomer of said serine derivative as the primary isomer thereof;
(b) transferring a portion of the aqueous L-erythro isomer containing phase produced in step (a) into an extraction vessel and extracting with an organic phase comprising (i) an aldehyde of the formula RCHO, wherein R is as set forth above, which may be the same or different than the aldehyde employed in step (a) in an amount effective to extract said L-serine derivative into said organic phase, or (ii) a mixture of said aldehyde and a water-immiscible organic solvent containing an amount of said aldehyde effective to extract said L-serine derivative isomer into said organic phase; and
(c) returning a portion of the aqueous phase of step (b) to said bioreactor;
(d) transferring a portion of the organic phase of step (b) into a reextraction vessel and extracting with an aqueous phase having a pH of less than about 7.0 to produce an aqueous solution of said L-serine derivative containing the L-erythro isomer as the primary isomer, the rates of extraction of steps (b) and (c) being greater than about one half the rate of total L-serine derivative synthesis in step (a).
(e) returning a portion of the organic phase of step (d) to said extraction vessel; and
(f) transferring a portion of the aqueous phase of step (d) containing said L-serine derivative to a product vessel,
wherein steps (a) through (f) are conducted continuously.

15. The process of claim 14, wherein the rates of extraction of steps (b) and (d) are about equal to or greater than the rate of total L-serine derivative synthesis in step (a).

16. The process of claim 15, wherein the extractions of steps (b) and (d) are conducted by countercurrently contacting the respective aqueous and organic phases.

17. The process of claim 15, wherein the concentration of glycine in step (a) is from about 100 to about 200 grams/liter; the concentration of aldehyde is from about 1 to about 10 grams/liter; the molar ratio of glycine to aldehyde is from about 15:1 to about 25:1; the pH of the aqueous solution is from about 8.5 to about 10; the temperature is from about 5 to 40° C.; the enzyme is present in an amount of from about 1,000 to about 1,000,000 units/liter; and pyridoxal-5-phosphate is present in an amount about equimolar to said enzyme.

18. The process of claim 17, further comprising the step of removing enzyme from the aqueous phase of step (a) prior to organic extraction in step (b).

19. The process of claim 18, wherein the organic phase of step (b) comprises a mixture of said solvent and from about 5 to 50% by volume of said aldehyde.

20. The process of claim 19, wherein said organic phase comprises a mixture of said aldehyde and a lower alkyl ester of a lower carboxylic acid or a mixture of said aldehyde, said lower alkyl ester of said lower carboxylic acid and an alcohol.

21. The process of claim 20, wherein said organic phase comprises (iii) a mixture of aldehyde and an ethyl, isopropyl butyl or isobutyl acetate, or (iv) mixtures of (iii) with butanol or benzyl alcohol.

22. The process of claims 15 or 18, wherein the pH of the aqueous phase of step (d) is less than about 5.0.

23. The process of claims 15 or 18, wherein the enzyme is serine hydroxymethyltransferase.

24. The process of claim 23, wherein said serine hydroxymethyltransferase is obtained from a genetically engineered microorganism containing a plasmid having inserted therein the *Escherichia coli glyA* gene.

25. The process of claims 14, 15, or 18, wherein the aldehyde is benzaldehyde and said L-serine derivative is L-erythro-phenylserine.

* * * * *